(12) United States Patent
Babaev

(10) Patent No.: US 7,878,991 B2
(45) Date of Patent: *Feb. 1, 2011

(54) PORTABLE ULTRASOUND DEVICE FOR THE TREATMENT OF WOUNDS

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 252 days.

This patent is subject to a terminal disclaimer.

(21) Appl. No.: 11/848,499

(22) Filed: Aug. 31, 2007

(65) Prior Publication Data

US 2008/0051693 A1 Feb. 28, 2008

Related U.S. Application Data

(63) Continuation-in-part of application No. 11/625,074, filed on Jan. 19, 2007, now abandoned, which is a continuation-in-part of application No. 11/467,382, filed on Aug. 25, 2006, now abandoned.

(51) Int. Cl.
*A61H 1/00* (2006.01)
(52) U.S. Cl. ............... 601/2; 600/2; 600/439; 604/22
(58) Field of Classification Search ........ 600/2, 600/439; 604/22; 601/2
See application file for complete search history.

(56) References Cited

U.S. PATENT DOCUMENTS

| | | | |
|---|---|---|---|
| 3,275,059 A | 9/1966 | McCullough | |
| 3,392,916 A | 7/1968 | Engstrom et al. | |
| 3,561,444 A | 2/1971 | Boucher | |
| 4,085,893 A | 4/1978 | Durley, III | |
| 4,153,201 A | 5/1979 | Berger et al. | |
| 4,251,031 A | 2/1981 | Martin et al. | |
| 4,294,407 A | 10/1981 | Reichl et al. | |
| 4,301,093 A | 11/1981 | Eck | |
| 4,301,968 A | 11/1981 | Berger et al. | |
| 4,309,989 A | 1/1982 | Fahim | |
| 4,352,459 A | 10/1982 | Berger et al. | |
| 4,428,531 A | 1/1984 | Martin | |
| 4,530,360 A | 7/1985 | Duarte | |
| 4,541,564 A | 9/1985 | Berger et al. | |
| 4,619,400 A | 10/1986 | Van Der Burgt | |
| 4,655,393 A | 4/1987 | Berger | |
| 4,659,014 A | 4/1987 | Soth et al. | |
| 4,679,551 A | 7/1987 | Anthony | |
| 4,726,523 A | 2/1988 | Kokubo et al. | |
| 4,726,525 A | 2/1988 | Yonekawa et al. | |
| 4,768,478 A | 9/1988 | Endo et al. | |
| 4,783,003 A | 11/1988 | Hirabayashi et al. | |
| 4,793,339 A | 12/1988 | Matsumoto et al. | |
| 4,850,534 A | 7/1989 | Takahashi et al. | |
| 4,877,989 A | 10/1989 | Drews et al. | |
| 4,930,700 A | 6/1990 | McKown | |
| 4,961,885 A | 10/1990 | Avrahami et al. | |

(Continued)

*Primary Examiner*—Long V Le
*Assistant Examiner*—Ellsworth Weatherby

(57) ABSTRACT

Device and methods for the treatment of wounds using ultrasound energy are disclosed. The portable wound treatment device may deliver ultrasound energy to a wound through direct contact with the ultrasound tip and/or through a liquid coupling medium. Several ultrasound tips specially designed to concentrate and focus ultrasound energy onto a wound are also disclosed. The ultrasound tip may also possess an abrasive peripheral boundary to aid in debriding the wound and/or removing necrotic tissue. The disclosed invention may have multiple beneficial effects in treating a wound such as sterilizing a wound, reducing external bleeding, and/or providing pain relief.

22 Claims, 3 Drawing Sheets

U.S. PATENT DOCUMENTS

| | | | |
|---|---|---|---|
| 5,002,059 A | 3/1991 | Crowley et al. |
| 5,063,922 A | 11/1991 | Hakkinen |
| 5,076,266 A | 12/1991 | Babaev |
| 5,104,042 A | 4/1992 | McKown |
| 5,134,993 A | 8/1992 | Van Der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,269,291 A | 12/1993 | Carter |
| 5,316,000 A | 5/1994 | Chapelon et al. |
| 5,318,014 A | 6/1994 | Carter |
| 5,362,309 A | 11/1994 | Carter |
| 5,380,411 A | 1/1995 | Schlief |
| 5,431,663 A | 7/1995 | Carter |
| 5,515,841 A | 5/1996 | Robertson et al. |
| 5,515,842 A | 5/1996 | Ramseyer et al. |
| 5,516,043 A | 5/1996 | Manna et al. |
| 5,545,124 A | 8/1996 | Krause et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,626,554 A | 5/1997 | Ryaby et al. |
| 5,643,179 A | 7/1997 | Fujimoto |
| 5,656,016 A | 8/1997 | Ogden |
| 5,707,402 A | 1/1998 | Heim |
| 5,735,811 A | 4/1998 | Brisken |
| 5,820,564 A * | 10/1998 | Slayton et al. ............... 600/459 |
| 5,835,678 A | 11/1998 | Li et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,947,921 A | 9/1999 | Johnson et al. |
| 6,007,499 A | 12/1999 | Martin et al. |
| 6,014,970 A | 1/2000 | Ivri et al. |
| 6,024,718 A | 2/2000 | Chen et al. |
| 6,102,298 A | 8/2000 | Bush et al. |
| 6,104,952 A | 8/2000 | Tu et al. |
| 6,106,547 A | 8/2000 | Huei-Jung |
| 6,113,558 A | 9/2000 | Rosenschein et al. |
| RE36,939 E | 10/2000 | Tachibana et al. |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,280,441 B1 | 8/2001 | Ryan |
| 6,283,986 B1 | 9/2001 | Johnson |
| 6,314,318 B1 | 11/2001 | Petty |
| 6,321,109 B2 | 11/2001 | Ben-Haim et al. |
| 6,322,527 B1 | 11/2001 | Talish |
| 6,325,769 B1 | 12/2001 | Klopotek |
| 6,478,754 B1 | 11/2002 | Babaev |
| 6,533,803 B2 | 3/2003 | Babaev |
| 6,569,099 B1 | 5/2003 | Babaev |
| 6,601,581 B1 | 8/2003 | Babaev |
| 6,623,444 B2 * | 9/2003 | Babaev ..................... 604/22 |
| 6,663,554 B2 | 12/2003 | Babaev |
| 6,685,656 B1 | 2/2004 | Durarte et al. |
| 6,723,064 B2 * | 4/2004 | Babaev ..................... 604/22 |
| 6,761,729 B2 | 7/2004 | Babaev |
| 6,799,729 B1 * | 10/2004 | Voic ..................... 239/102.2 |
| 6,916,296 B2 | 7/2005 | Soring et al. |
| 6,960,173 B2 | 11/2005 | Babaev |
| 6,964,647 B1 | 11/2005 | Babaev |
| 7,008,523 B2 | 3/2006 | Herrington |
| 7,025,735 B2 | 4/2006 | Soring et al. |
| 7,073,510 B2 | 7/2006 | Redmond et al. |
| 2001/0014780 A1 | 8/2001 | Martin et al. |
| 2002/0138036 A1 * | 9/2002 | Babaev ..................... 604/22 |
| 2003/0236560 A1 * | 12/2003 | Babaev ..................... 607/50 |
| 2004/0030254 A1 * | 2/2004 | Babaev ..................... 600/459 |
| 2004/0039418 A1 * | 2/2004 | Elstrom et al. ................ 607/3 |
| 2005/0261586 A1 | 11/2005 | Makin et al. |
| 2006/0036193 A1 | 2/2006 | Naraikin et al. |
| 2006/0058710 A1 | 3/2006 | Babaev |
| 2006/0173385 A1 * | 8/2006 | Lidgren et al. ................ 601/2 |
| 2006/0184071 A1 | 8/2006 | Klopotek |
| 2006/0235306 A1 | 10/2006 | Cotter |
| 2006/0241470 A1 * | 10/2006 | Novak et al. ................ 600/459 |
| 2006/0253050 A1 | 11/2006 | Yoshimine et al. |
| 2007/0060864 A1 | 3/2007 | Redding |
| 2007/0299369 A1 * | 12/2007 | Babaev ..................... 601/2 |

* cited by examiner

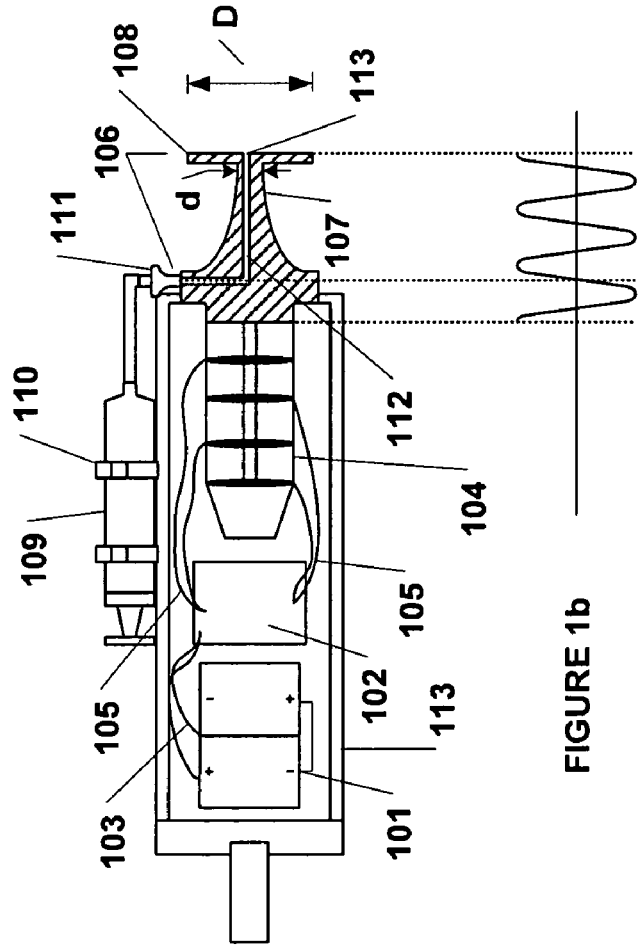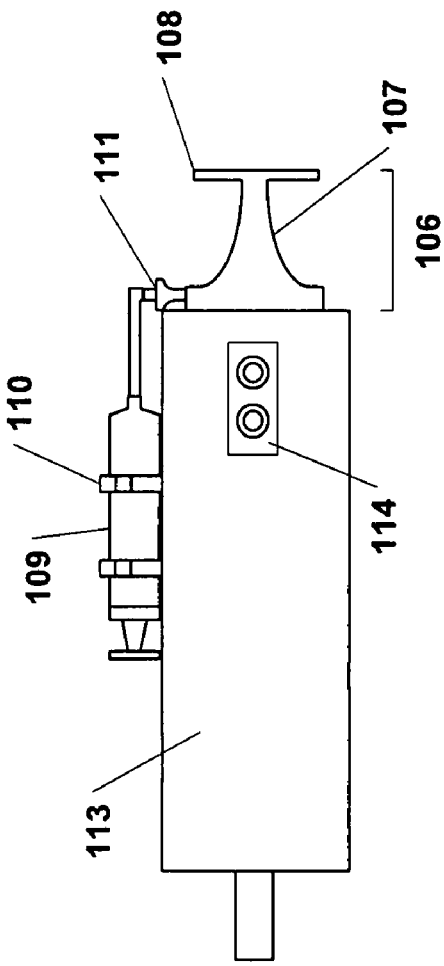
FIGURE 1a
FIGURE 1b
FIGURE 1c

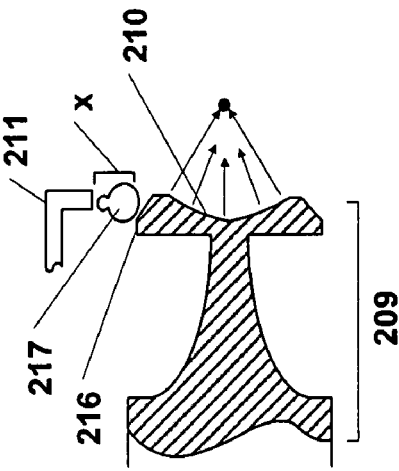
FIGURE 2e
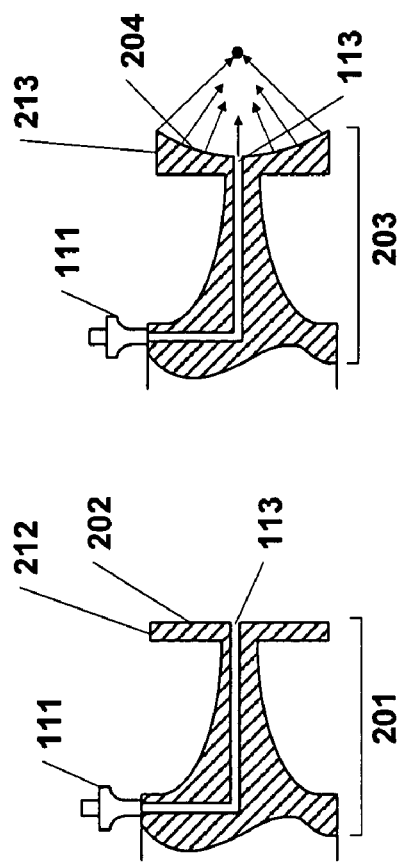
FIGURE 2b
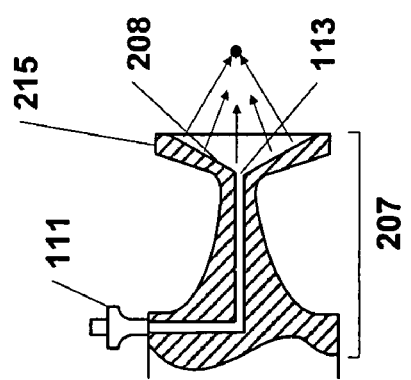
FIGURE 2d
FIGURE 2a
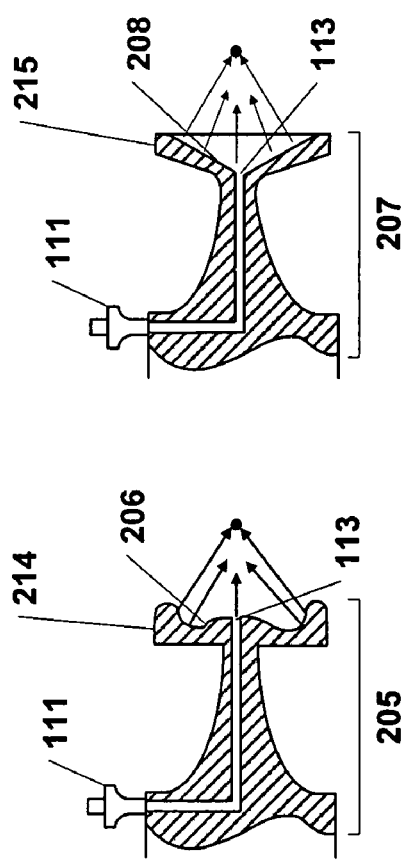
FIGURE 2c

PORTABLE ULTRASOUND DEVICE FOR THE TREATMENT OF WOUNDS

RELATED APPLICATIONS

This application claims the benefit of U.S. patent application Ser. No. 11/625,074 filed Jan. 19, 2007, which is a continuation-in-part of U.S. patent application Ser. No. 11/467,382 filed Aug. 25, 2006 both of which are now abandoned. Both applications are incorporated in there entirety herein.

BACKGROUND OF THE INVENTION

1. Field of the Invention

The present invention relates to a portable ultrasound wound treatment device for use in hospitals, doctors offices, ambulances, and/or for use by soldiers on a battlefield.

2. Description of the Related Art

There are a variety of known devices and methods for the treatment of wounds. These methods include wound dressings, hyperbaric oxygen treatment, growth factor therapy, antibiotics, surgery, physical therapy, vacuum therapy, electrical stimulation, bioengineered tissue, and ultraviolet light therapy. There are also a variety of known devices and methods for the treatment of wounds using ultrasound energy.

U.S. patents that disclose devices and methods for wound treatment using an ultrasound spray include: U.S. Pat. No. 6,478,754 to Babaev; U.S. Pat. No. 6,761,729 to Babaev; U.S. Pat. No. 6,533,803 to Babaev; U.S. Pat. No. 6,569,099 to Babaev; U.S. Pat. No. 6,663,554 to Babaev; and finally U.S. Pat. No. 6,960,173 to Babaev. These devices and methods can only achieve limited results because they fail to sufficiently deliver ultrasound energy due to a lack of direct contact with the target area. U.S. Pat. No. 7,025,735 to Soring and U.S. Pat. No. 6,916,296 also to Soring disclose a method and device for the treatment of septic wounds that uses both a liquid aerosol and direct contact. The Soring method and device, however, are not intended for use on fresh or acute wounds. U.S. Patent Application 2004/0030254 to Babaev discloses a device and method for ultrasound wound debridement through mechanical vibration in the ultrasound tip.

SUMMARY OF THE INVENTION

A portable device and methods for the treatment of wounds are disclosed. An embodiment of the portable device may comprise an ultrasound tip, an ultrasound transducer, a generator, a power supply, and a fluid supply. The ultrasound transducer, generator, and power source may be located within a housing member, and the ultrasound tip may protrude out of the outer casing/housing member. The ultrasound device may be powered by a battery or batteries and/or powered by an external power supply.

The ultrasound tip generally contains two portions: a concentrator portion and a radiation portion. The maximum diameter of the radiation portion may be approximately two or more times greater than the minimum diameter of the concentrator portion leading up to the radiation portion. A diameter ratio of this magnitude between the concentrator and the radiation portion is sufficient to ionize water and create free radicals. The point at which the concentrator portion connects to the radiation portion may lie on or near a nodal point of an ultrasound wave passing through the ultrasound tip. The distal end of the radiation portion may lie on or near an anti-nodal point of an ultrasound wave passing through the ultrasound tip. The shape of the distal end of the radiation portion may be concave, conical, a special concave-convex design, or a similar shape that allows for the ultrasound tip to focus ultrasound energy. A flat distal end radiation portion may also be utilized with the portable wound care device. The peripheral boundary of the radiation portion may include abrasive members to allow for the precise debridement of a wound and scrapping away of necrotic tissue. Examples of abrasive members include, but are not limited to, jagged teeth-like protrusions, a sharp edge, and a sandpaper-like material all of which are capable of scraping away at a surface.

Ultrasound energy may be delivered to a wound through a fluid coupling medium. The fluid coupling medium may be delivered through means external to the device. An example of external delivery would be application of a fluid coupling medium to the radiation portion, which would then be delivered to the wound. The fluid coupling medium may also be delivered through means internal to the device. Internal delivery may be achieved via a lumen located within the ultrasound tip originating in a fluid entry port and terminating in an orifice located on the distal end of the radiation portion of the ultrasound tip. The fluid entry point may lie on or near a nodal point of an ultrasound wave passing through the ultrasound tip. A fluid supply may be separate from and/or connected to the device. Fluids such as, but not limited to, tap water, distilled water, saline, antibiotics, and/or anti-inflammatories may be utilized with the device.

The disclosed device may focus ultrasound energy, mechanical energy, and a fluid coupling medium onto a wound. If fluids are introduced into the device at high pressures they may result in a jet stream spray pattern. If fluids are introduced at low pressures they may result in an atomized spray. Cavitations may be created in the coupling medium as it is delivered from the orifice onto the radiation portion and/or cavitations may be created in the coupling medium as it accumulates on the surface of the wound. Ultrasound energy may also be delivered to the wound through contact with the radiation portion.

Methods of wound treatment utilizing the disclosed device will vary according to the type and/or condition of the wound to be treated. It may be preferable to first deliver ultrasound energy at a distance from the wound via the fluid coupling medium. The ultrasonically activated fluid may irrigate the wound and provide for less painful treatment. After irrigation, it may be desirable to contact the wound with the ultrasound tip. The wound may be contacted with the distal end radiation portion of the ultrasound tip, but it is preferred to contact the wound with the peripheral boundary of the radiation portion, particularly when the peripheral boundary possesses abrasive members. The ultrasound tip may be moved across the surface of the wound in order to debride the wound and/or remove necrotic tissue. The method disclosed utilizes ultrasound energy from both the fluid coupling medium and the ultrasound tip, as well as mechanical energy to treat wounds.

BRIEF DESCRIPTION OF THE DRAWINGS

FIG. 1a is a cross-sectional view of an embodiment of the portable ultrasound device for the treatment of wounds.

FIG. 1b is a depiction of the propagation of ultrasound waves through the tip of the embodiment of the portable ultrasound device depicted in FIG. 1a.

FIG. 1c is a perspective view of the embodiment of the portable ultrasound device depicted in FIG. 1a.

FIG. 2a is a cross-sectional view of an embodiment of an ultrasound tip with a flat distal end radiation portion and a central orifice that may be used with the portable ultrasound device depicted in FIG. 1.

FIG. 2b is a cross-sectional view of an embodiment of an ultrasound tip with a concave distal end radiation portion and a central orifice that may be used with the portable ultrasound device depicted in FIG. 1.

FIG. 2c is a cross-sectional view of an embodiment of an ultrasound tip with a special concave-convex distal end radiation portion and a central orifice that may be used with the portable ultrasound device depicted in FIG. 1.

FIG. 2d is a cross-sectional view of an embodiment of an ultrasound tip with a conical distal end radiation portion and a central orifice that may be used with the portable ultrasound device depicted in FIG. 1.

FIG. 2e is a cross-sectional view of an embodiment of an ultrasound tip with a concave and a chamfer distal end radiation portion with no orifice that may be used with the portable ultrasound device depicted in FIG. 1.

DETAILED DESCRIPTION OF THE INVENTION

Figure 3C:
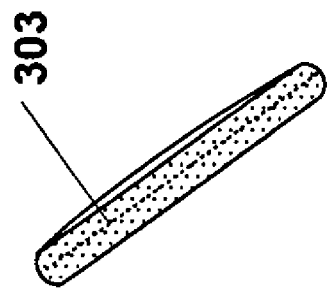
FIG. 3c is a cross-sectional view of an embodiment of the peripheral boundary of the ultrasound tip with a sandpaper-like surface that may be used with the portable ultrasound device depicted in FIG. 1.

Disclosed is a method and device for the treatment of wounds. Preferred embodiments of the disclosed device and methods are illustrated in the figures and described in detail below.

FIG. 1a is a cross-sectional view of an embodiment of the portable ultrasound wound treatment device. The embodiment comprises a power supply 101 connected to a generator 102 by electrical wires 103, a generator 102 connected to an ultrasound transducer 104 by electrical wires 105, and an ultrasound tip 106. The power supply 101 may be a battery or batteries, and said battery or batteries may be rechargeable. In the embodiment depicted, the power supply 101 is located within the device; in other embodiments the device may be connected to an external power source. The power supply 101 supplies electrical current to the generator 102 which supplies a signal of alternating voltage to drive the transducer 104. The transducer 104 converts the alternating voltage signal into mechanical motion within the ultrasound tip 106 which ultimately delivers ultrasound energy to the wound. The power supply 101, generator 102, transducer 104, and/or electrical wires 103 and 105 may be enclosed within an outer casing 113.

The ultrasound tip 106 comprises a concentrator portion 107 and a radiation portion 108. The proximal end of the concentrator portion 107 is in contact with transducer 104. The distal end of the concentrator portion 107 is in contact with the proximal end of the radiation portion 108. The maximum diameter D of the distal end of the radiation portion 108 should be greater than or equal to the minimum diameter d of the concentrator portion 107 leading up to the distal end of the radiation portion 108, with the diameter D approximately two-times or greater than diameter d. Diameter D is also preferably at least thirteen millimeters. The embodiment depicted also comprises a fluid supply 109. An exemplar fluid supply 109 is a syringe. The fluid supply 109 may be separate from the wound treatment device and/or it may be attached to the device. Fasteners 110 may be used to attach the fluid supply 109 to the wound treatment device. A fluid coupling medium may be delivered from the fluid supply 109 to a wound in several ways: fluid may be delivered directly from the fluid supply 109 to the distal end of radiation portion 108 of the ultrasound tip 106, and/or fluid may be delivered from the fluid supply 109 to an entry port 111 on the radial surface of the ultrasound tip 106 proximate to the concentrator portion 107. Fluid delivered to the fluid entry port 111 may travel through a lumen 112 located within the ultrasound tip 106 and ultimately be delivered to a wound through an orifice 113 in the distal end of the radiation portion 108 of the ultrasound tip 106. Preferably, the orifice 113 is centrally located on the distal end of the radiation portion 108. In the alternative or in combination, the fluid entry port 111 may be located on the proximal end of the device and/or the lumen 112 may originate in the proximal surface the ultrasound tip 106 and terminate in the orifice 113. Fluids such as, but not limited to, tap water, distilled water, saline, antibiotics, and/or anti-inflammatories, may be utilized.

FIG. 1b is a depiction of the propagation of the amplitude of the ultrasound waves passing through the ultrasound tip of the embodiment described above. The fluid entry port 111 and the point where the distal end of the concentrator portion 107 contacts the proximal end of the radiation portion 108 may lie on or near nodal points. The distal end of the radiation portion 108 may lie on or near an anti-nodal point.

FIG. 1c is a perspective view of the embodiment depicted in FIG. 1a. As illustrated, the device may also comprise a power switch 114 located on outer casing 113.

FIGS. 2a-FIG. 2e depict various embodiments of ultrasound tips that may be used with the embodiment depicted in FIG. 1. FIG. 2a depicts an ultrasound tip 202 with a radiation portion 212 comprising a flat distal end 202, a fluid supply port 111, and an orifice 113. FIG. 2b depicts an ultrasound tip 203 with a radiation portion 213 comprising a concave distal end 204, a fluid supply port 111, and an orifice 113. FIG. 2c depicts an ultrasound tip 205 with a radiation portion 214 comprising a concave-convex designed distal end 206, a fluid supply port 111, and an orifice 113. FIG. 2d depicts an ultrasound tip 207 with a radiation portion 215 comprising a conical distal end 208, a fluid supply port 111, and an orifice 113. FIG. 2e depicts an ultrasound tip 209 with a radiation portion 216 comprising a concave distal end 210 with a chamfer for convenient external delivery of a fluid. In the depicted embodiment, fluid is delivered directly to the distal end 210 of the radiation portion 216 from exit port 211. Preferably, the distance x between the exit port 211 and the distal end 210 of the radiation portion 216 of the ultrasound tip 209 should be less than the diameter of the liquid drop 217 delivered from the exit port 211.

Figure 3B:
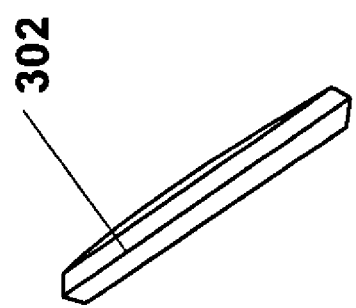
FIG. 3b is a cross-sectional view of an embodiment of the peripheral boundary of the ultrasound tip with a sharp cutting edge that may be used with the portable ultrasound device depicted in FIG. 1.
Figure 3A:
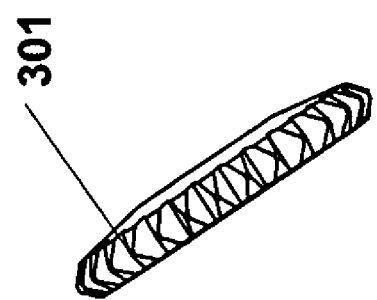
FIG. 3a is a cross-sectional view of an embodiment of the peripheral boundary of the ultrasound tip with jagged teeth-like protrusions that may be used with the portable ultrasound device depicted in FIG. 1.

FIGS. 3a-3c depict various embodiments of abrasive peripheral edges that may be used with the ultrasound tips depicted in FIGS. 2a-2e. The abrasive peripheral edges depicted may be used in the alternative or in combination. FIG. 3a depicts an embodiment of an ultrasound tip comprising a peripheral boundary with teeth-like protrusions 301. FIG. 3b depicts an embodiment of an ultrasound tip comprising a sharp cutting edge 302. FIG. 3c depicts an embodiment of an ultrasound tip comprising a sandpaper-like surface 303. The abrasive peripheral edges depicted allow for precise debridement of a wound and the scrapping away of unwanted surface tissue.

In a method of wound treatment, ultrasound energy is first delivered at a distance from the wound through a fluid coupling medium. The ultrasonically activated fluid coupling medium may irrigate the wound and allow for less painful treatment of the wound. After irrigation, the ultrasound tip may come into contact with the wound. The wound may be contacted with the distal end of the radiation portion of the ultrasound tip, but it is preferred to contact the wound with the abrasive peripheral boundary. The ultrasound device may be moved longitudinally to remove necrotic tissue with the abrasive peripheral boundary, while continually debriding and ultrasonically treating the wound. The device may be moved in a single direction or it can be moved back-and-forth. The manner in which ultrasound energy is delivered may depend on the type and/or condition of the wound being treated.

The intensity of the ultrasound energy may be controlled through variations in the ultrasound parameters, such as frequency, amplitude, and treatment time. The intensity of the ultrasound energy should be at least 0.1 watt/cm$^2$. The preferred intensity range is approximately 1 watt/cm$^2$-10 watt/cm$^2$ and the more preferred intensity range is approximately 1 watt/cm$^2$-2 watt/cm$^2$. The recommended intensity of the ultrasound energy is approximately 2 watt/cm$^2$. The transducer may operate in a frequency range of 20 kHz to 40 MHz. The preferred frequency range in which the transducer operates is 30 kHz-50 kHz, and the recommend frequency value in which the transducer operates is 30 kHz. The transducer may displace at an amplitude of at least 1 micron. The preferred amplitude range is approximately 5 microns-150 microns with a more preferred amplitude range of approximately 60 microns-80 microns. The recommended amplitude value is approximately 80 microns. The generator may be capable of generating a continuous, pulsed, fixed, and/or modulated frequency depending on the wound to be treated. The generator may also be capable of generating different types of wave forms such as, but not limited to, sinusoidal, rectangular, trapezoidal and triangular.

It should be appreciated that elements described with singular articles such as "a", "an", and/or "the" and/or otherwise described singularly may be used in plurality. It should also be appreciated that elements described in plurality may be used singularly.

Although specific embodiments of apparatuses and methods have been illustrated and described herein, it will be appreciated by those of ordinary skill in the art that any arrangement, combination, and/or sequence of that is calculated to achieve the same purpose may be substituted for the specific embodiments shown. It is to be understood that the above description is intended to be illustrative and not restrictive. Combinations of the above embodiments and other embodiments as well as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. A portable ultrasound device for treating wounds, comprising:
    a. A power supply;
    b. A generator electrically connected to said power supply;
    c. An ultrasound transducer containing a distal end, electrically connected to said generator;
    d. An ultrasound tip attached to the distal end of said ultrasound transducer comprising:
        i. A proximal concentrator portion, having a longitudinal axis, in contact with said transducer, said concentrator portion tapering toward a smallest cross section at it's distal end;
        ii. A distal end radiation portion oriented substantially perpendicular to said longitudinal axis of said concentrator portion containing a peripheral boundary, said distal end radiation portion projecting radially from the distal end of said concentrator portion, with a maximum diameter approximately 2 times or greater than the diameter of said smallest cross section of said concentrator portion; and
    e. A fluid supply capable of delivering a fluid to the radiation portion.

2. The device according to claim 1, further characterized by said transducer being capable of operating at a frequency range of approximately 20 kHz-40 MHz.

3. The device according to claim 1, further characterized by said transducer being capable of operating at a preferred frequency range of approximately 30 kHz-50 kHz.

4. The device according to claim 1, further characterized by said transducer being capable of operating at a recommended frequency value of approximately 30 kHz.

5. The device according to claim 1, further characterized by said transducer being capable of displacing an amplitude of at least 1 micron.

6. The device according to claim 1, further characterized by said transducer being capable of displacing a preferred amplitude range approximately 5 microns-150 microns.

7. The device according to claim 1, further characterized by said transducer being capable of displacing a most preferred amplitude range approximately 60 microns-80 microns.

8. The device according to claim 1, further characterized by said transducer being capable of displacing at an amplitude value of approximately 80 microns.

9. The device according to claim 1, further comprising a lumen within said ultrasound tip originating in a radial surface of said ultrasound tip and opening at an orifice within said distal end radiation portion capable of receiving fluid from said fluid supply.

10. The device according to claim 1, further comprising a lumen within said ultrasound tip originating in a proximal surface of said ultrasound tip and opening at an orifice within said distal end radiation portion capable of receiving fluid from said fluid supply.

11. The device according to claim 9, further characterized by a fluid entry port connecting said fluid supply with said lumen.

12. The device according to claim 10, further characterized by a fluid entry port connecting said fluid supply with said lumen.

13. The device according to claim 1, further characterized by diameter of said distal end radiation portion being approximately thirteen millimeters.

14. The device according to claim 1, further characterized by said radiation portion having a rough peripheral boundary.

15. The device according to claim 1, further characterized by said ultrasound tip having a flat distal end radiation portion.

16. The device according to claim 1, further characterized by said ultrasound tip having a concave shaped distal end radiation portion.

17. The device according to claim 1, further characterized by said ultrasound tip having an outer concave portion adjacent to an inner convex portion on the distal end radiation portion.

18. The device according to claim 1, further characterized by said ultrasound tip having a conical shaped distal end radiation portion.

19. The device according to claim 1, further characterized by said generator being capable of generating a continuous or pulsed frequency.

20. The device according to claim 1, further characterized by said generator being capable of generating a fixed or modulated frequency.

21. The device according to claim 1, further characterized by said generator being capable of generating a wave form which is selected from the group consisting of sinusoidal, rectangular, trapezoidal and triangular wave forms.

22. A method for treating wounds, comprising the steps of:
   a. Providing an ultrasound tip comprising:
      i. A concentrator portion having a longitudinal axis, said concentrator portion tapering toward a smallest cross section at it's distal end;
      ii. A distal end radiation portion oriented substantially perpendicular to said longitudinal axis of the concentrator portion with abrasive members, said distal end radiation portion projecting radially from the distal end of said concentrator portion, with a maximum diameter approximately 2 times or greater than the diameter of said smallest cross section of said concentrator portion; and
   b. Providing a fluid supply capable of delivering a fluid coupling medium to the radiation surface;
   c. Delivering ultrasound energy from said ultrasound tip through said fluid coupling medium;
   d. Contacting a target with said peripheral boundary of said radiation portion of said ultrasound tip;
   e. Delivering ultrasound energy through direct contact of said ultrasound tip to said target; and
   f. Moving said ultrasound tip.

* * * * *